United States Patent

Hoffmann et al.

(10) Patent No.: US 8,168,576 B2
(45) Date of Patent: May 1, 2012

(54) VOLUME GIVING CLEANSING COMPOSITION

(75) Inventors: Martin Hoffmann, Zwingenberg (DE); Diana Leukel-Schäfer, Darmstadt (DE)

(73) Assignee: KAO Germany GmbH, Darmstadt (DE)

( * ) Notice: Subject to any disclaimer, the term of this patent is extended or adjusted under 35 U.S.C. 154(b) by 0 days.

(21) Appl. No.: 13/024,968

(22) Filed: Feb. 10, 2011

(65) Prior Publication Data

US 2011/0126850 A1  Jun. 2, 2011

Related U.S. Application Data

(62) Division of application No. 12/420,375, filed on Apr. 8, 2009, now abandoned.

(30) Foreign Application Priority Data

Apr. 15, 2008 (EP) ..................... 08007353

(51) Int. Cl.
  *C11D 9/26* (2006.01)
  *C11D 1/00* (2006.01)
  *C11D 1/72* (2006.01)
  *C11D 3/20* (2006.01)

(52) U.S. Cl. ........ 510/119; 510/153; 510/155; 510/421; 510/437; 510/505; 424/401; 424/502; 424/70.19

(58) Field of Classification Search ............ 510/119, 510/153, 155, 421, 437, 505; 424/401, 502, 424/70.19
See application file for complete search history.

(56) References Cited

U.S. PATENT DOCUMENTS 5,792,739 A * 8/1998 He et al. ............. 510/422

FOREIGN PATENT DOCUMENTS

| EP | 1034775 | * | 9/2000 |
| EP | 1034775 | A | 9/2000 |
| EP | 1656967 | * | 5/2006 |
| EP | 1656967 | A | 5/2006 |
| EP | 1714678 | A | 10/2006 |
| WO | 97/40125 | A | 10/1997 |
| WO | 2004/024110 | A | 3/2004 |

* cited by examiner

*Primary Examiner* — Brian P Mruk
(74) *Attorney, Agent, or Firm* — Norris McLaughlin & Marcus, PA

(57) ABSTRACT

The present invention is related to an aqueous cleansing composition especially for keratin fibers such as human hair with excellent volume enhancing effect. First object of the present invention is a cleansing composition for hair comprising at least one surfactant selected from anionic, non-ionic and amphoteric ones and furthermore comprising at least one ethoxylated monoglyceride according to the general formula

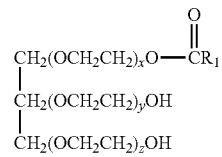

wherein $R_1$ is a saturated or unsaturated and branched or straight alkyl chain with a chain length of 7 to 21 C atoms and $x+y+z$ has a value of 3 to 200 and at least one (poly)propylene glycol according to the following formula

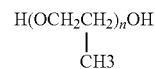

wherein n has a value between 1 and 70.

15 Claims, No Drawings

VOLUME GIVING CLEANSING COMPOSITION

This is a divisional application of U.S. Ser. No. 12/420,375, which was filed on Apr. 8, 2009, now abandoned, and claims the priority to European Application No. 08007353.9-1521, filed on Apr. 15, 2008.

The present invention is related to an aqueous cleansing composition for keratin fibres especially human hair with excellent volume enhancing effect.

Cleansing compositions have been known for many years. Many patent applications and scientific publications deal with such compositions aiming at cleansing and especially improved conditioning effects wherein volume enhancing effect of human hair has gained particular attention. Although this, there is still need for improvement.

Hair volume is especially an aggravated problem for people with fine hair. All shampoo compositions comprise conditioning ingredients which are deposited to hair surface during washing process and improve various properties of hair such as combability, shine and elasticity. High level of conditioning ingredients is especially needed for damaged hair which is due to environmental effects and/or chemical hair dressing cycles lost its natural smooth surface structure. Very often, for fine hair, and especially fine and damaged hair, there is a loss of hair volume because of these conditioning ingredients contained in shampoo compositions. Therefore, there is highly need for new compositions which condition hair in a usual way but does not cause loss of volume.

In order to solve volume problem, people with fine hair use often hair styling compositions which simply fixes hair at a style by hardening on hair surface after application. This has, however, a big disadvantage as hair does not feel soft and natural upon touching.

The aim of the present invention is providing cleansing compositions for hair which gives hair volume and body and at the same time provides hair good conditioning effects with improved combability, elasticity, shine and manageability.

Present inventors have surprisingly found out that a cleansing composition based one or more surfactants and comprising an ethoxylated monogylceride and a polypropylene glycol provides hair excellent volume and body with good hair conditioning effect.

Therefore, first object of the present invention is a cleansing composition for hair comprising at least one surfactant selected from anionic, non-ionic and amphoteric ones and furthermore comprising at least one ethoxylated monoglyceride according to the general structure

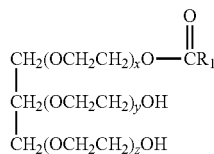

wherein $R_1$ is a saturated or unsaturated and branched or straight alkyl chain with a chain length of 7 to 21 C atoms and x+y+z has a value of 3 to 200 and at least one (poly)propylene glycol according to the following formula

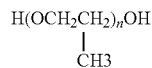

wherein n has a value between 1 and 70.

Within the meaning of the present invention, with the term ethoxylated monoglyceride compounds according to the above formula are meant.

Second object of the present invention is the use of a cleansing composition based on at least one surfactant selected from anionic, non-ionic and amphoteric ones and comprising at least one ethoxylated monoglyceride of the above formula and at least one (poly)propylene glycol for increasing hair volume and body.

Cleansing composition of the present invention comprises at least one ethoxylated monoglyceride according to the above general formula. In the preferred embodiment of the present invention $R_1$ is a saturated or unsaturated and branched or straight alkyl chain with a chain length of 11 to 17 C atoms, more preferably 13 to 17 C atoms and most preferably 15 to 17 C atoms and x+y+z has preferably a value of 10 to 150, more preferably 20 to 100 and most preferably 40 to 90.

Ethoxalted monogylcerides are known for their thickening ability in the area of hair cleansing compositions. For example WO 03/063818 A1 discloses ethoxylated glycerides as thickening agents in combination with ethoxylated fatty alcohol and ethoxylated partial gylcerides. WO 2004/024110 A1 and WO 03/013467 A1 disclose cleansing compositions comprising an ethoxylated monogylceride. The compositions in the latter two publications are free from polypropylene glycol especially the ones will be mentioned as preferred compounds below.

Non-limiting suitable examples of ethoxylated monoglycerides are PEG-6 glyceryl caprate, PEG-3 glyceryl cocoate, PEG-7 glyceryl cocoate, PEG-30 glyceryl cocoate, PEG-40 glyceryl cocoate, PEG-78 glyceryl cocoate, PEG-80 glyceryl cocoate, PEG-3 glyceryl isostearate, PEG-5 glyceryl isostearate, PEG-6 glyceryl isostearate, PEG-8 glyceryl isostearate, PEG-9 glyceryl isostearate, PEG-10 glyceryl isostearate, PEG-15 glyceryl isostearate, PEG-20 glyceryl isostearate, PEG-25 glyceryl isostearate, PEG-30 glyceryl isostearate, PEG-40 glyceryl isostearate, PEG-50 glyceryl isostearate, PEG-60 glyceryl isostearate, PEG-90 glyceryl isostearate, PEG-7 glyceryl laurate, PEG-8 glyceryl laurate, PEG-12 glyceryl laurate, PEG-15 glyceryl laurate, PEG-20 glyceryl laurate, PEG-23 glyceryl laurate, PEG-30 glyceryl laurate, PEG-5 glyceryl oleate, PEG-10 glyceryl oleate, PEG-15 glyceryl oleate, PEG-20 glyceryl oleate, PEG-25 glyceryl oleate, PEG-30 glyceryl oleate, PEG-15 glyceryl ricinoleate, PEG-20 glyceryl ricinoleate, PEG-5 glyceryl sesquioleate, PEG-7 glyceryl soyate, PEG-30 glyceryl soyate, PEG-5 glyceryl stearate, PEG-10 glyceryl stearate, PEG-15 glyceryl stearate, PEG-20 glyceryl stearate, PEG-25 glyceryl stearate, PEG-30 glyceryl stearate, PEG-40 glyceryl stearate, PEG-60 glyceryl stearate, PEG-120 glyceryl stearate, PEG-200 glyceryl stearate, PEG-28 glyceryl tallowate, PEG-80 glyceryl tallowate, PEG-82 glyceryl tallowate, PEG-130 glyceryl tallowate and PEG-200 glyceryl tallowate.

Among the ethoxylated monogylcerides, with fatty acid chain of laurate, isostearate, oleate and stearate are preferred. More preferred are with fatty acid chain of isostearate, oleate and stearate. The most preferred are with fatty acid chain of isostearate and stearate. Especially preferred is with fatty acid chain of isostearate.

The especially preferred ethoxylated monoglyceride is PEG-90 glyceryl isostearate which is available from Zschimmer & Schwarz under the trade name Oxetal VD 92.

Concentration of ethoxylated monoglyceride in the compositions of the present invention is in the range of 0.1 to 20%, preferably 0.25 to 15%, more preferably 0.5 to 10% and most preferably 1 to 7.5% by weight, calculated to total composition.

Composition of the present invention comprises at least one (poly)propylene glycol of the above formula. Non-limiting suitable examples are PPG-3, PPG-7, PPG-9, PPG-12, PPG-13, PPG-15, PPG-16, PPG-17, PPG-20, PPG-26, PPG-30, PPG-33, PPG-34, PPG-51 and PPG-69. Preferred are PPG-3, PPG-7, PPG-9, PPG-12, PPG-13, PPG-15, PPG-16, PPG-17, PPG-20, PPG-26, PPG-30, PPG-33 and PPG-34. More preferred polypropylene glycols are PPG-7, PPG-9, PPG-12, PPG-13, PPG-15, PPG-16, PPG-17, PPG-20, PPG-26 and PPG-30. Most preferred ones are PPG-7, PPG-9, PPG-12, PPG-13, PPG-15, PPG-16, PPG-17 and PPG-20. Especially preferred one is PPG-9 with which most of the experiments were carried out.

Concentration of at least one (poly)propylene glycol of the above formula in compositions of the present invention is in the range of 0.1 to 10%, more preferably 0.25 to 7.5%, and most preferably 0.5 to 5% by weight, calculated to total composition.

In the preferred embodiment of the present invention ethoxylated monoglyceride of the above formula and (poly)propylene glycol of the above formula are contained in the compositions of the present invention at a weight ratio of ethoxylated monoglyceride to (poly)propylene glycol in the range of 20:1 to 1:10, preferably 15:1 to 1:5, more preferably 10:1 to 1:3 and most preferably 5:1 to 1:1.

Cleansing compositions of the present invention comprise at least one surfactant selected from anionic, non-ionic and/or amphoteric or zwitterionic surfactants at a concentration range of 5 to 50%, preferably 5 to 40% and more preferably 7.5 to 30%, and most preferably 10 to 25% by weight, calculated to the total composition.

In an embodiment of the present invention, cleansing composition of the present invention, comprises at least one anionic, at least one nonionic surfactant. More preferably the compositions further comprise additionally at least one amphoteric surfactant.

Anionic surfactants suitable within the scope of the invention are preferably present in an amount from 1 to about 30%, preferably 2 to 20% and most preferably 2-15%, and most preferably 2 to 10% by weight, calculated to the total composition.

In principal any anionic surfactant is suitable within the meaning of the present invention. Nonlimiting examples are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

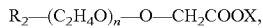

wherein $R_2$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

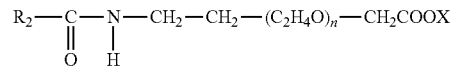

wherein $R_2$ and X have the above meanings, and n is in particular a number from 1 to 10, preferably 2.5 to 5.

Such products have been known for some time and are on the market, for example, under the trade name "AKYPO®" and AKYPO-SOFT®.

Also useful are $C_8$-$C_{20}$-acyl isethionates, alone or in admixture with other anionic surfactants, as well as sulfofatty acids and the esters thereof.

It is also possible to use mixtures of several anionic surfactants, for example an ether sulfate and a polyether carboxylic acid or alkyl amidoether carboxylic acid.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, cocoyl glutamate preferably in form of the water-soluble alkali or ammonium, in particular the sodium salts thereof, preferably in admixture with the above-named anionic surfactants.

The most preferred anionic surfactants within the meaning of the present invention are those of alkyl ether sulphates such as lauryl ether sulphate and aminocarboxylic acids such as lauroyl glutamate sodium salt.

Further surfactants in the shampoo compositions according to the invention are nonionic surfactants especially in admixture with anionic surfactants. Especially suited are alkyl polyglucosides of the general formula

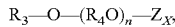

wherein $R_3$ is an alkyl group with 8 to 18 carbon atoms, $R_4$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 1% to 15%, in particular from 1% to 10% by weight, calculated to the total composition.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components may be present, for example, long-chain fatty acid dialkanolamides, such as coco fatty acid diethanolamide and myristic fatty acid diethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides which may be present in an amount from 0.25% to 5% by weight, calculated to the total composition. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl)amineoxides, or also amineoxides with ethyleneoxide and/or propyleneoxide groups in the alkyl chain. Such amineoxides are on the market, for example, under the trade names Ammonyx®, "Aromox®" or Genaminox®.

Further nonionic surfactants useful in the compositions according to invention are $C_{10}$-$C_{22}$-fatty alcohol ethoxylates at a concentration of 0.5 to 10%, preferably 0.5 to 5% by weight, calculated to total composition. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

The most preferred non-ionic surfactants are alkyl polyglucosides such as decyl, cocoyl polyglucoside and ethoxylated fatty alcohols such as laureth-16.

As further surfactant component, the compositions according to the invention can also contain amphoteric or zwitterionic surfactants, for example in an amount from about 0.5% to about 15%, preferably from about 1% to about 10%, by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

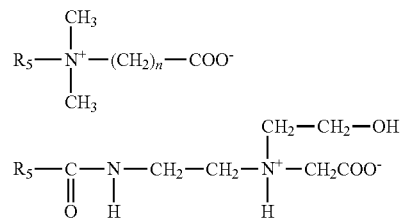

wherein $R_5$ is a $C_8$-$C_{18}$-alkyl group and n is 1 to 3; sulfobetaines of the structure

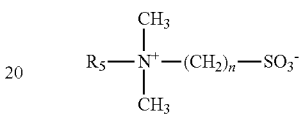

wherein $R_5$ and n are same as above; and amidoalkyl betaines of the structure

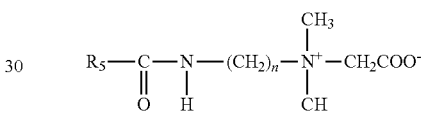

wherein $R_5$ and n are same as above.

The most preferred amphoteric surfactants are alkyl betaines such as lauryl betaine and alkyl amido betaines such as cocamidopropyl betaine.

In the preferred form of the present invention, cleansing composition comprises at least one anionic surfactant especially of alkyl ether sulphate type, at least one amphoteric surfactant especially alkyl amido alkyl betaine type and at least one non-ionic surfactant especial an alkyl polyglucoside. In the most preferred form of the present invention, in addition to the above mentioned surfactant the composition comprises additionally acyl amido carboxylic acid surfactant especially sodium lauroyl glutamate.

The composition of the present invention comprises hair-conditioning agents. Conditioning agents can be selected from oily substances, non-ionic substances, cationic amphiphilic ingredients, cationic polymers or their mixtures.

Oily substances are selected from such as silicone oils, either volatile or non-volatile, natural and synthetic oils. Among silicone oils those can be added to the compositions include dimethicone, dimethiconol, polydimethylsiloxane, DC fluid ranges from Dow Corning, arylated silicones such as phenyl trimethicone or any other silicone with up to 5 aryl, preferably phenyl, group in its molecule, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $$R_6CO(OCH_2CH_2)_nOH$$

or $$R_6CO(OCH_2CH_2)_nOOCR_7$$

where $R_6$ and $R_7$ are independent from each other saturated, unsaturated or branched or non-branched alkyl chain with 7 to 21 C atoms and n is typically 2-100.

In one of the preferred form of the present invention, coloring enhancing cleansing compositions comprise at least one cationic polymer as conditioning agent. Suitable cationic polymers are those of best known with their CTFA category name Polyquaternium. Typical examples of those are Polyquaternium 1, Polyquaternium 2, Polyquaternium 4, Polyquaternium 5, Polyquaternium 6, Polyquaternium 7, Polyquaternium 8, Polyquaternium 9, Polyquaternium 10, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 24, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

It has further been found out that especially those of cationic cellulose type polymers known as Polymer JR type from Amerchol such as Polyquaternium 10 or cationic galactomannans such as cationic guar gum known with trade name Jaguar from Rhône-Poulenc which are chemically for example Guar hydroxypropyl trimonium chloride and cationic tara gum an its derivatives known with INCI name Caesalpinia spinosa hydroxypropyltrimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, cationic Caesalpinia spinosa gum derivatives, polyquaternium 6, polyquaternium 7, polyquaternium 67 and polyquaternium 70.

The cationic polymers also include the quaternized products of graft polymers from organopolysiloxanes and polyethyl oxazolines described in EP-A 524 612 and EP-A 640 643.

Although less preferred cleansing compositions of the present invention may comprise additionally one or more cationic surfactant(s) as conditioner presented with the general formula $$R_{11}-\overset{R_8}{\underset{R_{10}}{N^+}}-R_9 \ X^-$$

where $R_8$ is a saturated or unsaturated, branched or non-branched alkyl chain with 8-22 C atoms or $$R_{12}CONH(CH_2)_n$$

where $R_{12}$ is saturated or unsaturated, branched or non-branched alkyl chain with 7-21 C atoms and n has value of 1-4, or $$R_{13}COO(CH_2)_n$$

where $R_{13}$ is saturated or unsaturated, branched or non-branched alkyl chain with 7-21 C atoms and n has value of 1-4, and $R_9$ is hydrogen or unsaturated or saturated, branched or non-branched alkyl chain with 1-22 C atoms or $$R_{12}CONH(CH_2)_n$$

or $$R_{13}COO(CH_2)_n$$

where $R_{12}$, $R_{13}$ and n are same as above.

$R_{10}$ and $R_{111}$ are hydrogen or lower alkyl chain with 1 to 4 carbon atoms, and X is anion such as chloride, bromide, methosulfate.

Typical examples of those ingredients are cetyl trimethly ammonium chloride, stear trimonium chloride, behentrimoinium chloride, stearamidopropyl trimonuim chloride, dioleoylethyl dimethyl ammonium methosulfate, dioleoylethyl hydroxyethylmonium methosulfate.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Typical concentration range for any of those conditioners of cationic polymers, silicon oil and derivatives and cationic surfactants can be 0.01-5% by weight, preferably 0.01-3.5% by weight, more preferably 0.05-2.5% and most preferably 0.1-1.5% by weight calculated to the total composition. Most preferred conditioning agents are cationic polymers.

Further conditioning additives are hair conditioning and/or styling polymers. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water- or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives.

Amphoteric polymers are found to be useful in conditioning shampoo composition of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomere®"; copolymers from methacryl oylethyl betaine and alkyl methacrylates of the type "Yukaformer®", e.g., the butyl methacrylate copolymer "Yukaformer® Am75"; copolymers from monomers containing carboxyl groups and sulfonic groups, e.g., (meth)acrylic acid and itaconic acid, with monomers such as mono- or dialkyl amino alkyl(meth)acrylates or mono- or dialkyl aminoalkyl (meth)acrylamides containing basic groups, in particular amino groups; copolymers from N-octyl acryl-amide, methyl methacrylate, hydroxypropyl methacrylate, N-tert.-butyl aminoethyl-methacrylate and acrylic acid, as well as the copolymers known from U.S. Pat. No. 3,927,199, are applicable.

Cleansing composition of the present invention can be transparent as well as pearly. Transparency of the composition is judged by naked eye in a transparent shampoo bottle with a thickness not more than 5 cm. In the case a transparent appearance is wished, the following ingredients are not essential. Pearl-shiny appearance is achieved with those dispersed in cleansing conditioning compositions in crystalline form, i.e. so called pearl-shine or pearlizing agents. The preferred once are PEG-3 distearate and ethylene glycol distearate. The concentration of those can typically be from 0.1 to 3%, preferably 0.5 to 2% by weight, calculated to the total composition. These compounds are preferably added to the compositions in admixture with anionic, nonionic and/or amphoteric surfactants. Such kinds of mixtures are available commercially.

Solubilizers may be added to the compositions especially when oily substances are chosen as conditioning agents and fragrance oils with highly lipophilic properties. Typical solubilizers may be hydrogenated castor oil known with the trade mark Cremophor CO series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

The cleansing composition may contain active ingredients selected from UV filters, moisturisers, sequestering agents, and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are preferably selected from polycarboxy acids. The preferred one is ethylene diamine tetraacetic acid, EDTA. Typical useful concentration range for sequestering agents is of 0.01-2.5% by weight calculated to the total composition.

The UV filters are that oil and water soluble ones for the purpose of protecting hair colour. In other words, anionic and nonionic, oily, UV filters are suitably used in the compositions of the present invention. Suitable UV-absorbing substances is are: 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4, 4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzylidenecampher, 3-(4'-sulfo)-benzyl-idenebornane-2-one and the salts thereof, 3-(4'-methyl benzylidene)-DL-campher, and/or polysilicone-15. The amount of the UV-absorber ranges typically from about 0.01% to 2.5%, more preferably from 0.05% to 1% by weight, calculated to the total composition.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, coconut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, various "Extrapone®" products, and "Herbasol®". Extracts and the preparation thereof are also described in "Hagers Handbuch der pharmazeutischen Praxis", $4^{th}$ Ed.

Compositions of the present invention may comprise further at least one compound according to the formula

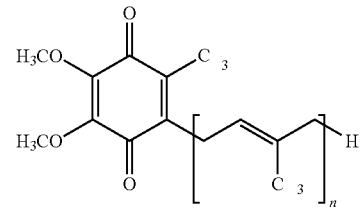

where n is a number between 1 and 10.

The compounds of the above formula are known as Ubiquinone, and also are known as Coenzyme. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

Cleansing compositions of the present invention can also comprise synthetic mica as a further shine enhancer.

Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference. It also discloses a cleansing composition comprising monoethanolamide surfactant in addition to other surfactants.

Suitable metal oxide or oxides for coating synthetic mica are titanium dioxide, chromium oxide, ferric oxide or mixtures thereof. In the present invention the preferred is synthetic mice coated with titanium dioxide. Such materials are commercially available from Sun Chemical Corporation and known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.20 to 2.5% by weight calculated to total composition.

Further in preferred embodiment of the present invention, compositions comprise at least one direct dye. Suitable direct dyes are of cationic, anionic and neutral nitro dyes. It should be noted that they can also be used in combination with each other. In other words a composition according to present invention can comprise an anionic and a cationic dye as well as an anionic and a nitro dye or a cationic and a nitro dye. Certainly the combination of all three dyestuffs is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 5% by weight, preferably 0.01 to 4% more preferably 0.05 to 3% and most preferably 0.1 to 2.5% by weight calculated to total composition.

Cleansing compositions of the present invention can be in the form of conventional liquid thickened shampoo, as well in the form of ready to use foam, delivered either from a pump-foamer or from an aerosol bottle. In the case that an aerosol foam preparation is preferred, propellant gas must be added to the formulation. The suitable propellant gasses are carbondioxide, dimethylether and alkanes such as butane propane or their mixtures.

The viscosity of the cleansing compositions according to the invention is in the range of 500 and about 20,000 mPa·s at 20° C., preferably 1,000 to 10,000, in particular 1,000 to 7,000 mPa·s at 20° C., measured with Brookfield or Höppier viscosimeters at a shear rate of 10 sec$^{-1}$.

Viscosity of shampoo compositions can be adjusted with known viscosity enhancers. The preferred ones are monoglycerides such as glyceryl laurate, oleate, and PEG-18 glyceryl oleate/cocoate known with the trade names Antil® 141 and 171, respectively and PEG-160 sorbitan triisostearate known with a trade name Rheodol®. It should be noted that in the case that a composition are delivered in the form of a foam from a pump-foamer and/or aerosol can, those compositions should not be thickened and have a viscosity value not more than 500 mPa·s, more preferably 250 mPa·s measured as mentioned above at room temperature.

Since one of the claimed ingredients is also known as thickener, in another preferred embodiment of the present invention is that cleansing composition for hair based on at least one surfactant and further comprising at least one ethoxylated monogylceride and at least one (poly)propylene glycol wherein the composition does not comprise any other thickening agent.

It is self-understood that the shampoos according to the invention may comprise other substances customarily used in such compositions such as preservatives, fragrances.

The pH of the compositions according to the present invention is suitably between 2 and 8.0, preferably in the range of 2.5 to 7.0, more preferably 3 to 6.5 and most preferably 4 to 5.5 measured at ambient temperature with a suitable pH meter.

pH of the compositions is adjusted with acidic and alkaline compounds. Acidic compounds can be inorganic and organic acid or their mixtures. Nonlimiting suitable examples are citric acid, lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. Alkaline compounds such as sodium hydroxide can be used to adjust the pH of the compositions.

The following examples are to illustrate the invention, but not to limit. The products according to the invention are prepared by mixing the individual components in water, whereby it is also possible to use pre-mixtures of various ingredients.

EXAMPLE 1

|  | % by weight |
| --- | --- |
| Sodium lauryl ether sulphate | 8.0 |
| Cocoyl polyglucoside | 3.0 |
| Cocamidopropyl betaine | 3.0 |
| Sodium lauroyl glutamate | 1.0 |
| Trimethyl pentaphenyl trisiloxane | 0.2 |
| Polyquaternium-10 | 1.0 |
| PEG-90 glyceryl isostearate | 3.5 |
| PPG-9 | 0.7 |
| Citric acid/sodium hydroxide | q.s. to pH 5.5 |
| Preservative, fragrance | q.s |
| Water | to 100 |

For the comparative purposes the above composition was also prepared without PEG-90 glyceryl isostearate and PPG-9. Both compounds were replaced largely by water and partly by sodium chloride which was used to increase the viscosity.

The performance of the above example was compared to the comparative composition in a half side test with 10 volunteers. Hair of the volunteer was divided into 2 and washed with example 1 and comparative composition using according to hair length 4 to 6 g of the product. After rinsing both sides were evaluated by at least 2 hair dressers and by the volunteer in towel dried and dry state. It was found that the side washed with example 1 had significantly more volume and body and furthermore more elasticity and shine. The preferences were generally 9 to 1 and for volume 10/0.

Similar results were observed with the examples below.

EXAMPLE 2

|  | % by weight |
| --- | --- |
| Sodium lauryl ether sulphate | 8.0 |
| Laureth - 16 | 4.0 |
| Cocamidopropyl betaine | 3.0 |
| Sodium lauroyl glutamate | 1.0 |
| Polyquaternium-7 | 1.0 |
| PEG-90 glyceryl isostearate | 5.0 |
| PPG-9 | 1.0 |
| Citric acid/sodium hydroxide | q.s. to pH 5.5 |
| Preservative, fragrance | q.s |
| Water | to 100 |

The above composition increases hair volume, improves combability and shine.

EXAMPLE 3

|  | % by weight |
| --- | --- |
| Sodium lauryl ether carboxylate | 9.0 |
| Laureth - 16 | 3.0 |
| Cocoyl betaine | 2.0 |
| Sodium lauroyl glutamate | 2.0 |
| Polyquaternium-6 | 0.5 |
| Dimethicone | 0.5 |
| Ubiquinone | 0.1 |
| PEG-90 glyceryl isostearate | 4.0 |
| PPG-9 | 2.0 |
| Citric acid/sodium hydroxide | q.s. to pH 5.0 |
| Preservative, fragrance | q.s |
| Water | to 100 |

The above composition improves hair volume, gives hair more elasticity.

EXAMPLE 4

|  | % by weight |
| --- | --- |
| Sodium lauryl ether sulphate | 8.0 |
| Cocoyl polyglucoside | 3.0 |
| Cocoamphoacetate | 4.0 |
| Polyquaternium-7 | 0.8 |
| Dimethicone | 0.5 |
| PEG-90 glyceryl isostearate | 5.0 |
| PPG-9 | 1.2 |
| Basic red 51 | 0.1 |
| Citric acid/sodium hydroxide | q.s. to pH 5.5 |
| Preservative, fragrance | q.s |
| Water | to 100 |

Above composition gives hair a red shine, in addition to the increasing volume.

EXAMPLE 5

|  | % by weight |
| --- | --- |
| Sodium lauryl ether sulfate | 9.0 |
| Laureth - 16 | 3.0 |
| Cocoyl betaine | 2.0 |
| Sodium lauroyl glutamate | 2.0 |
| Guarhydroxypropyltrimonium chloride | 1.0 |
| PEG-90 glyceryl isostearate | 2.0 |
| PPG-9 | 1.0 |
| Trimethyl pentaphenyl trisiloxane | 0.3 |
| Basic yellow 87 | 0.08 |
| Basic red 76 | 0.001 |
| Citric acid/sodium hydroxide | q.s. to pH 5.0 |
| Preservative, fragrance | q.s |
| Water | to 100 |

Increase of volume and an excellent golden blonde shine was observed on light blond hair.

EXAMPLE 6

| | % by weight |
|---|---|
| Sodium lauryl ether sulfate | 9.0 |
| Laureth - 16 | 3.0 |
| Cocoyl betaine | 2.0 |
| Sodium lauroyl glutamate | 2.0 |
| Guarhydroxypropyltrimonium chloride | 1.0 |
| PEG-90 glyceryl isostearate | 2.0 |
| PPG-9 | 1.0 |
| Trimethyl pentaphenyl trisiloxane | 0.3 |
| Basic red 51 | 0.1 |
| Basic orange 31 | 0.05 |
| Citric acid/sodium hydroxide | q.s. to pH 5.0 |
| Preservative, fragrance | q.s |
| Water | to 100 |

Increase of volume and an excellent red shine were observed on medium blond hair.

EXAMPLE 7

| | % by weight |
|---|---|
| Sodium lauryl ether sulfate | 9.0 |
| Laureth - 16 | 3.0 |
| Cocoyl betaine | 2.0 |
| Sodium lauroyl glutamate | 2.0 |
| Polyquaternium-10 | 1.0 |
| PEG-90 glyceryl isostearate | 3.5 |
| PPG-9 | 0.7 |
| Carbopol Aqua CC | 5.0 |
| Synthetic fluorphologopite | 0.5 |
| Citric acid/sodium hydroxide | q.s. to pH 4.7 |
| Preservative, fragrance | q.s |
| Water | to 100 |

* Synthetic fluorphologopite used is commercially available from Sun Chemical Corporation under the trade name SunShine Glitter White with a particle size distribution in the range of 20 to 95 µm.

EXAMPLE 8

| | % by weight |
|---|---|
| Sodium lauryl ether sulfate | 10.0 |
| Cocoyl betaine | 2.0 |
| Sodium lauroyl glutamate | 2.0 |
| Quaternium 80 | 0.5 |
| PEG-90 glyceryl isostearate | 4.5 |
| PPG-9 | 1.7 |
| Citric acid/sodium hydroxide | q.s. to pH 5.0 |
| Preservative, fragrance | q.s |
| Water | to 100 |

Above shampoo was found to be excellent volume giving shampoo in a half side test carried out in a similar way as described above for example 1.

EXAMPLE 9

| | % by weight |
|---|---|
| Sodium lauryl ether sulphate | 8.0 |
| Cocoyl polyglucoside | 2.0 |
| Cocamidopropyl betaine | 4.0 |
| Sodium lauroyl glutamate | 2.0 |
| Trimethyl pentaphenyl trisiloxane | 0.3 |
| Polyquaternium-7 | 1.0 |
| PEG-120 glyceryl stearate | 3.0 |
| PPG-15 | 1.7 |
| Citric acid/sodium hydroxide | q.s. to pH 5.2 |
| Preservative, fragrance | q.s |
| Water | to 100 |

Above shampoo was found to be excellent in volume enhancing effect. Additionally it improves combability and showed excellent shine enhancing effect.

EXAMPLE 10

| | % by weight |
|---|---|
| Sodium lauryl ether sulphate | 8.0 |
| Laureth - 16 | 5.0 |
| Cocamidopropyl betaine | 4.0 |
| Polyquaternium-7 | 1.0 |
| PEG-90 glyceryl isostearate | 2.5 |
| PEG-30 glyceryl isostearate | 2.5 |
| PPG-15 | 0.3 |
| PPG-9 | 0.8 |
| Citric acid/sodium hydroxide | q.s. to pH 5.2 |
| Preservative, fragrance | q.s |
| Water | to 100 |

The above composition increases hair volume, improves combability and shine.

EXAMPLE 11

| | % by weight |
|---|---|
| Sodium lauryl ether carboxylate | 9.0 |
| Laureth - 16 | 3.0 |
| Cocoyl betaine | 2.0 |
| Sodium lauroyl glutamate | 2.0 |
| Polyquaternium-6 | 0.5 |
| Dimethicone | 0.5 |
| Ubiquinone | 0.1 |
| PEG-60 glyceryl isostearate | 4.0 |
| PPG-9 | 2.0 |
| Citric acid/sodium hydroxide | q.s. to pH 5.0 |
| Preservative, fragrance | q.s |
| Water | to 100 |

The above composition improves hair volume, gives hair more elasticity and shine

EXAMPLE 12

|  | % by weight |
| --- | --- |
| Sodium lauryl ether sulphate | 8.0 |
| Cocoyl polyglucoside | 3.0 |
| Cocoamphoacetate | 4.0 |
| Cocoyl betaine | 1.0 |
| Polyquaternium-7 | 0.8 |
| Dimethicone | 0.5 |
| PEG-90 glyceryl isostearate | 3.0 |
| PPG-12 | 0.6 |
| PPG-7 | 0.9 |
| Basic red 51 | 0.1 |
| Citric acid/sodium hydroxide | q.s. to pH 5.5 |
| Preservative, fragrance | q.s |
| Water | to 100 |

Above composition gives hair a red shine, in addition to the increasing volume.

EXAMPLE 13

|  | % by weight |
| --- | --- |
| Sodium lauryl ether sulfate | 9.0 |
| Laureth-16 | 3.0 |
| Cocoyl betaine | 2.0 |
| Sodium lauroyl glutamate | 2.0 |
| Guarhydroxypropyltrimonium chloride | 1.0 |
| PEG-80 glyceryl cocoate | 4.0 |
| PPG-20 | 0.8 |
| Trimethyl pentaphenyl trisiloxane | 0.2 |
| Basic yellow 87 | 0.10 |
| Basic red 76 | 0.01 |
| Citric acid/sodium hydroxide | q.s. to pH 5.0 |
| Preservative, fragrance | q.s |
| Water | to 100 |

Increase of volume and an excellent golden blonde shine was observed on light blond hair.

EXAMPLE 14

|  | % by weight |
| --- | --- |
| Sodium lauryl ether sulfate | 9.0 |
| Laureth-16 | 3.0 |
| Cocoyl betaine | 2.0 |
| Sodium lauroyl glutamate | 2.0 |
| Guarhydroxypropyltrimonium chloride | 1.0 |
| PEG-120 glyceryl stearate | 1.8 |
| PPG-7 | 1.8 |
| Dimethicone | 1.0 |
| Basic red 51 | 0.1 |
| Basic orange 31 | 0.05 |
| Citric acid/sodium hydroxide | q.s. to pH 5.0 |
| Preservative, fragrance | q.s |
| Water | to 100 |

Increase of volume and an excellent red shine were observed on medium blond hair.

The invention claimed is:

1. A method of increasing volume of hair, the method comprising:
preparing a cleansing composition comprising at least one surfactant selected from anionic, non-ionic and amphoteric ones at a concentration of 5 to 50% by weight calculated to total composition, wherein the cleansing composition comprises at least one ethoxylated monoglyceride according to the general formula

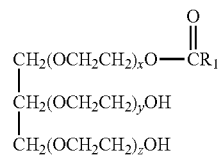

wherein $R_1$ is a saturated or unsaturated and branched or straight alkyl chain with a chain length of 7 to 21 C atoms and x+y+z has a value of 3 to 200, wherein the at least one ethoxylated monoglyceride is selected from PEG-6 glyceryl caprate, PEG-3 glyceryl cocoate, PEG-7 glyceryl cocoate, PEG-30 glyceryl cocoate, PEG-40 glyceryl cocoate, PEG-78 glyceryl cocoate, PEG-80 glyceryl cocoate, PEG-3 glyceryl isostearate, PEG-5 glyceryl isostearate, PEG-6 glyceryl isostearate, PEG-8 glyceryl isostearate, PEG-9 glyceryl isostearate, PEG-10 glyceryl isostearate, PEG-15 glyceryl isostearate, PEG-20 glyceryl isostearate, PEG-25 glyceryl isostearate, PEG-30 glyceryl isostearate, PEG-40 glyceryl isostearate, PEG-50 glyceryl isostearate, PEG-60 glyceryl isostearate, PEG-90 glyceryl isostearate, PEG-7 glyceryl laurate, PEG-8 glyceryl laurate, PEG-12 glyceryl laurate, PEG-15 glyceryl laurate, PEG-20 glyceryl laurate, PEG-23 glyceryl laurate, PEG-30 glyceryl laurate, PEG-5 glyceryl oleate, PEG-10 glyceryl oleate, PEG-15 glyceryl oleate, PEG-20 glyceryl oleate, PEG-25 glyceryl oleate, PEG-30 glyceryl oleate, PEG-15 glyceryl ricinoleate, PEG-20 glyceryl ricinoleate, PEG-5 glyceryl sesquioleate, PEG-7 glyceryl soyate, PEG-30 glyceryl soyate, PEG-5 glyceryl stearate, PEG-10 glyceryl stearate, PEG-15 glyceryl stearate, PEG-20 glyceryl stearate, PEG-25 glyceryl stearate, PEG-30 glyceryl stearate, PEG-40 glyceryl stearate, PEG-60 glyceryl stearate, PEG-120 glyceryl stearate, PEG-200 glyceryl stearate, PEG-28 glyceryl tallowate, PEG-80 glyceryl tallowate, PEG-82 glyceryl tallowate, PEG-130 glyceryl tallowate and PEG-200 glyceryl tallowate, and at least one (poly)propylene glycol according to the general formula

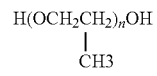

wherein n has a value between 1 and 70, wherein the at least one (poly)propylene glycol is selected from PPG-3, PPG-7, PPG-9, PPG-12, PPG-13, PPG-15, PPG-16, PPG-17, PPG-20, PPG-26, PPG-30, PPG-33, PPG-34, PPG-51 and PPG-69; and
increasing the volume of the hair by washing the hair with the cleansing composition and rinsing the cleansing composition from the hair.

2. The method according to claim 1, wherein the cleansing composition further comprises at least one anionic surfactant and at least one non-ionic surfactant.

3. The method according to claim 2, wherein the cleansing composition further comprises at least one amphoteric surfactant.

4. The method according to claim 1, wherein x+y+z in the general formula of ethoxylated monoglyceride has a value of 20 to 150.

5. The method according to claim 1, wherein R1 in the general formula of ethoxylated monoglyceride is selected from isostearate and stearate.

6. The method according claim 1, wherein ethoxylated monoglyceride is PEG-90 glyceryl isostearate.

7. The method according to claim 1, wherein ethoxylated monoglyceride and (poly)propylene glycol are comprised at a weight ratio of ethoxylated monoglyceride and (poly)propylene glycol in the range of 20:1 to 1:10.

8. The method according to claim 1, wherein the cleansing composition further comprises at least one conditioning agent.

9. The method according to claim 8, wherein conditioning agent is a cationic compound.

10. The method according to claim 8, wherein the at least one conditioning agent is a silicone compound.

11. The method according to claim 1, wherein the cleansing composition further comprises at least one UV filter.

12. The method according to claim 1, wherein the cleansing composition further comprises at least one direct dye.

13. The method according to claim 1, wherein the step of preparing the cleansing composition further comprises:
    mixing the at least one surfactant selected from anionic, non-ionic and amphoteric surfactants, the at least one ethoxylated monoglyceride and the at least one (poly)propylene glycol in water.

14. The method according to claim 1, wherein the at least one (poly)propylene glycol is selected from PPG-3, PPG-7, PPG-9, PPG-12, PPG-13, PPG-15, PPG-16, PPG-17, PPG-20, PPG-26, PPG-30, PPG-33 and PPG-34.

15. The method according to claim 9, wherein the conditioning agent is a cationic polymer.

* * * * *